(12) United States Patent
Thistle

(10) Patent No.: US 7,993,334 B2
(45) Date of Patent: Aug. 9, 2011

(54) LOW-PROFILE, EXPANDING SINGLE NEEDLE ABLATION PROBE

(75) Inventor: Robert C. Thistle, Bridgewater, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 662 days.

(21) Appl. No.: 11/322,439

(22) Filed: Dec. 29, 2005

(65) Prior Publication Data

US 2007/0156130 A1 Jul. 5, 2007

(51) Int. Cl.
*A61B 18/14* (2006.01)
(52) U.S. Cl. .......................................... 606/41; 606/45
(58) Field of Classification Search .................. 600/373;
606/41, 47; 607/127
See application file for complete search history.

(56) References Cited

U.S. PATENT DOCUMENTS

| | | | | |
|---|---|---|---|---|
| 4,976,711 | A * | 12/1990 | Parins et al. | 606/48 |
| 5,279,299 | A | 1/1994 | Imran | |
| 5,406,946 | A | 4/1995 | Imran | |
| 5,972,026 | A * | 10/1999 | Laufer et al. | 607/96 |
| 6,004,269 | A | 12/1999 | Crowley et al. | |
| 6,322,559 | B1 * | 11/2001 | Daulton et al. | 606/41 |
| 6,379,353 | B1 | 4/2002 | Nichols | |
| 6,488,673 | B1 * | 12/2002 | Laufer et al. | 604/516 |
| 2003/0159700 | A1 | 8/2003 | Laufer et al. | |
| 2004/0059404 | A1 * | 3/2004 | Bjorklund et al. | 607/126 |
| 2004/0230123 | A1 * | 11/2004 | White et al. | 600/466 |

FOREIGN PATENT DOCUMENTS

| | | |
|---|---|---|
| WO | WO 96/29946 A1 | 10/1996 |
| WO | WO 01/19270 | 3/2001 |
| WO | WO 02/102255 | * 12/2002 |
| WO | WO 2005/070491 | * 8/2005 |

OTHER PUBLICATIONS

PCT International Search Report dated Oct. 9, 2007 for related International Application Serial No. PCT/US2006/062036 filed Dec. 13, 2006, Inventor Robert C. Thistle (4 pages).
PCT Written Opinion dated Oct. 9, 2007 for related International Application Serial No. PCT/US2006/062036 filed Dec. 13, 2006, Inventor Robert C. Thistle (6 pages).
International Preliminary Report on Patentability (Chapter I of the Patent Cooperation Treaty) issued by The International Bureau for PCT/US2006/062036, Applicant: Boston Scientific Scimed, Inc., dated Jul. 10, 2008 (7 pages).

* cited by examiner

*Primary Examiner* — Linda C Dvorak
*Assistant Examiner* — Jaymi Della
(74) *Attorney, Agent, or Firm* — Vista IP Law Group LLP

(57) ABSTRACT

Tissue ablation probes, systems, and methods are provided for treating tissue (e.g., a tumor). The probe comprises an inner probe shaft, and an outer probe shaft disposed around the inner probe shaft. The outer probe shaft has a distal portion fixably mounted to the inner probe shaft, and a proximal portion rotatably mounted to the inner probe shaft. The probe further comprises a coiled ablation electrode disposed between the proximal portion and the distal portion. The electrode is configured for unwinding when the proximal portion rotates about the inner probe shaft in one direction, thereby placing the electrode in a radially expanded geometry, and configured for winding when the proximal portion rotates about the inner probe shaft in another opposite direction, thereby placing the electrode in a radially collapsed geometry.

20 Claims, 7 Drawing Sheets

LOW-PROFILE, EXPANDING SINGLE NEEDLE ABLATION PROBE

FIELD OF THE INVENTION

The field of the invention relates generally to the structure and use of radio frequency (RF) electrosurgical probes for the treatment of tissue.

BACKGROUND OF THE INVENTION

The delivery of radio frequency (RF) energy to target regions of solid tissue is known for a variety of purposes of particular interest to the present inventions. In one particular application, RF energy may be delivered to diseased regions (e.g., tumors) in target tissue for the purpose of tissue necrosis. RF ablation of tumors is currently performed within one of two core technologies.

The first technology uses a single needle electrode, which when attached to a RF generator, emits RF energy from the exposed, uninsulated portion of the electrode. This energy translates into ion agitation, which is converted into heat and induces cellular death via coagulation necrosis. In theory, RF ablation can be used to sculpt precisely the volume of necrosis to match the extent of the tumor. By varying the power output and the type of electrical waveform, it is possible to control the extent of heating, and thus, the resulting ablation. The diameter of tissue coagulation from a single electrode, however, has been limited by heat dispersion. As a result, multiple probe insertions have been required to treat all but the smallest lesions. This considerably increases treatment duration and requires significant skill for meticulous precision of probe placement. Increasing generator output has been unsuccessful for increasing lesion diameter, because an increased wattage is associated with a local increase of temperature to more than 100° C., which induces tissue vaporization and charring. This then increases local tissue impedance, limiting RF deposition, and therefore heat diffusion and associated coagulation necrosis.

The second technology utilizes multiple needle electrodes, which have been designed for the treatment and necrosis of tumors in the liver and other solid tissues. PCT application WO 96/29946 and U.S. Pat. No. 6,379,353 disclose such probes. In U.S. Pat. No. 6,379,353, a probe system comprises a cannula having a needle electrode array reciprocatably mounted therein. The individual electrodes within the array have spring memory, so that they assume a radially outward, arcuate configuration as they are advanced distally from the cannula. In general, a multiple electrode array creates a larger ablation area than that created by a single needle electrode. Some medical personnel, however, still prefer to use single needle electrodes, either because they feel more comfortable with single needle electrodes, find it difficult to accurately deploy multiple electrode arrays, and/or are concerned that one or more of the multiple needle electrodes, which are mounted to the probe with one connection, may break off in the tumor.

There, thus, remains a need to provide a single electrode ablation probe that can create larger ablation area.

SUMMARY OF THE INVENTION

In accordance with a first aspect of the present inventions, a probe for ablating tissue (e.g., a tumor) is provided. The probe comprises an inner probe shaft, and an outer probe shaft disposed around the inner probe shaft. In one embodiment, the inner probe shaft is rigid, so that the ablation probe can be percutaneously introduced into the tissue. The inner probe shaft may further comprise a tissue penetrating tip to facilitate its percutaneous introduction into the tissue. The outer probe shaft has a distal portion fixably mounted to the inner probe shaft, and a proximal portion rotatably mounted to the inner probe shaft. The probe further comprises a coiled ablation electrode disposed between the proximal portion and the distal portion. In one embodiment, the proximal and distal portions of the outer probe shaft and the electrode form a unibody design.

The electrode is configured for unwinding when the proximal portion rotates about the inner probe shaft in one direction, thereby placing the electrode in a radially expanded geometry, and configured for winding when the proximal portion rotates about the inner probe shaft in another opposite direction, thereby placing the electrode in a radially collapsed geometry. In an optional embodiment, the proximal portion of the outer probe shaft may be configured to longitudinally translate in a proximal direction relative to the inner probe shaft to, e.g., allow the windings of the expanded ablation electrode to have an open pitch to place the ablation electrode in a longitudinally expanded geometry. In one embodiment, the electrode is configured for unwinding in response to rotation of the proximal portion of the outer probe shaft in the one direction, and configured for winding in response to rotation of the proximal portion in the other direction. The electrode may have a shaped memory corresponding to the radially expanded geometry, thereby facilitating radially expansion of the ablation electrode. The probe may further comprise an electrical connector electrically coupled to the electrode. The ablation electrode may optionally comprise an elongated element that has a width pitched relative to the longitudinal axis of the ablation electrode, whereby a leading edge of the coiled element is configured to cut through solid tissue as the ablation electrode is placed in the radially expanded geometry.

In an optional embodiment, the inner probe shaft has a medial portion disposed between the proximal and distal portions. In this case, the electrode may be disposed between the proximal portion and the medial portion of the outer probe shaft, and the probe may further comprise another coiled ablation electrode disposed between the medial portion and the distal portion of the outer probe shaft. The other electrode is configured for unwinding when the proximal portion rotates about the inner probe shaft in the one direction, thereby placing the other electrode in a radially expanded geometry, and configured for winding when the proximal portion rotates about the inner probe shaft in the other opposite direction, thereby placing the other electrode in a radially collapsed geometry.

In accordance with a second aspect of the present inventions, a tissue ablation system is provided. The tissue ablation system comprises the previously described probe, and a radio frequency (RF) source operably coupled to the electrode.

In accordance with a third aspect of the present inventions, a method of treating tissue (e.g., a tumor) is provided. The method comprises introducing (e.g., percutaneously) the previously described probe into contact with the tissue while the electrode is in the radially collapsed geometry, placing the electrode in the radially expanded geometry, and conveying radio frequency (RF) energy from the expanded electrode, thereby creating an ablation lesion within the tissue. The electrode can be placed in the radially expanded geometry by rotating the proximal portion of the outer probe shaft in the one direction. The electrode can optionally be placed into the longitudinally expanded geometry by displacing the proximal shaft portion in the proximal direction relative to the inner probe shaft.

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE PREFERRED EMBODIMENTS

Figure 1:
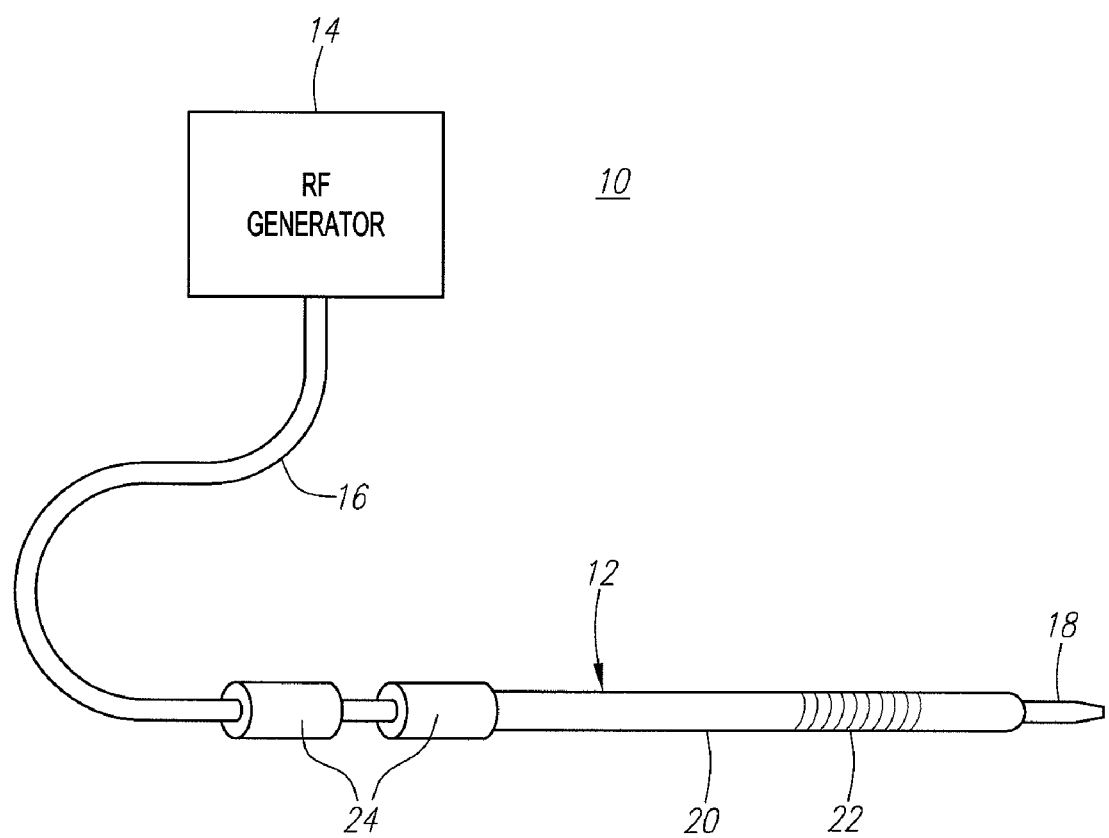
FIG. 1 is a plan view of a tissue ablation system constructed in accordance with one preferred embodiment of the present inventions.

FIG. 1 illustrates a tissue ablation system 10 constructed in accordance with a preferred embodiment of the present inventions. The tissue ablation system 10 generally comprises a tissue ablation probe 12 configured for introduction into the body of a patient for ablative treatment of target tissue, and a radio frequency (RF) generator 14 configured for supplying RF energy to the ablation probe 12 via an RF cable 16 in a controlled manner. The ablation probe 12 generally comprises an inner probe shaft 18, an outer probe shaft 20 disposed around the inner probe shaft 18, a coiled ablation electrode 22, and a handle assembly 24.

Figure 2:
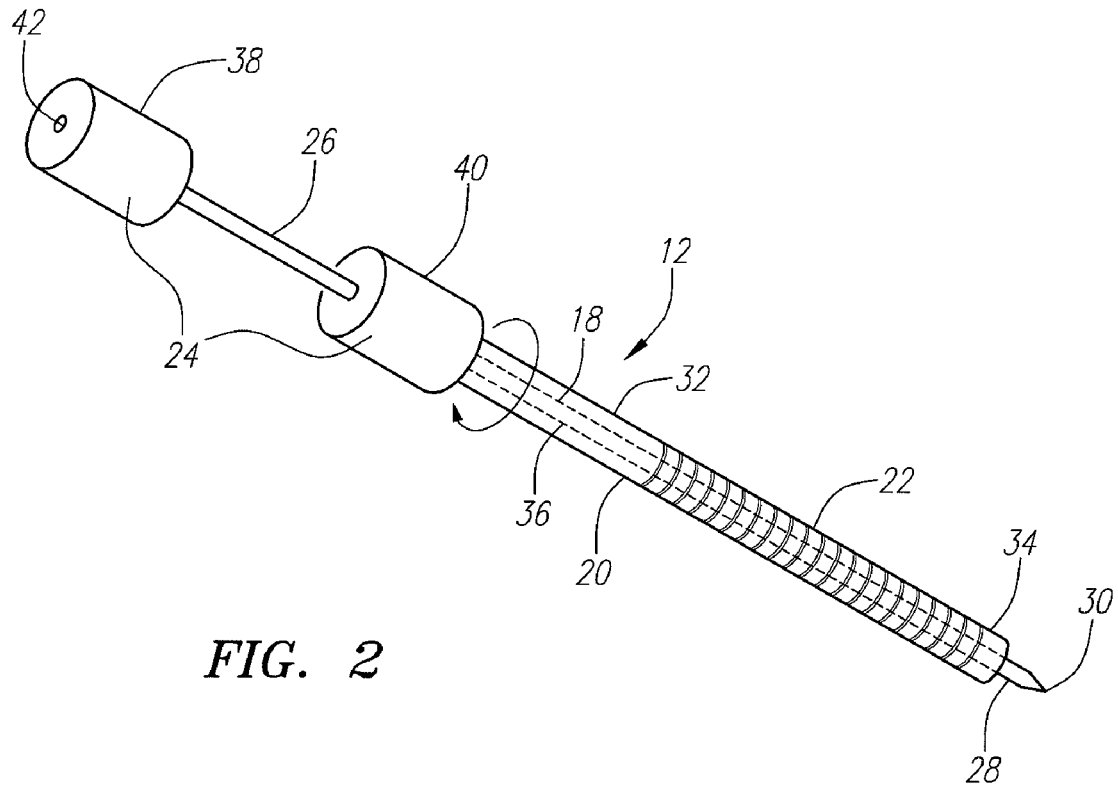
FIG. 2 is a perspective view of a tissue ablation probe used in the tissue ablation system of FIG. 1, wherein an ablation electrode is particularly shown in a low-profile collapsed geometry.
Figure 3:
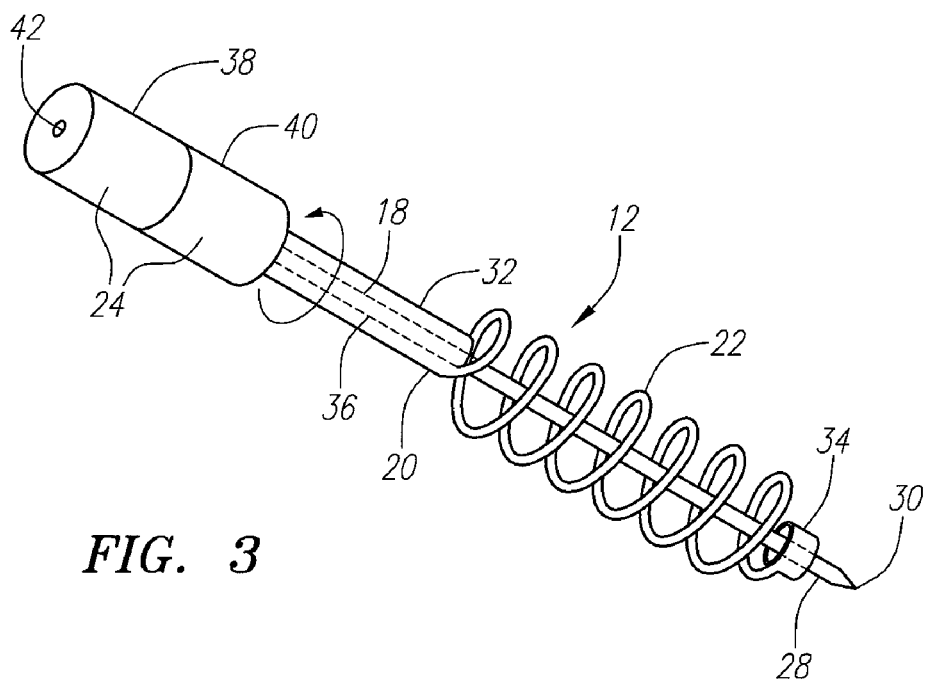
FIG. 3 is a perspective view of the tissue ablation probe of FIG. 2, wherein the ablation electrode is particularly shown in an expanded geometry.

Referring further to FIGS. 2 and 3, the inner probe shaft 18 has a proximal end 26 and a distal end 28. In the illustrated embodiment, the inner probe shaft 18 is rigid and has a tissue penetrating tip 30 to facilitate percutaneous introduction of the ablation probe 12 into the targeted tissue region. Alternatively, the inner probe shaft 18 may be semi-rigid or flexible, in which case, the outer probe shaft 20 or another device can be used to percutaneously introduce the ablation probe 12 into contact with the targeted tissue region. The inner probe shaft 18 is composed of a suitable material, such as plastic, metal or the like, and has a suitable length, typically in the range from 5 cm to 30 cm, preferably from 10 cm to 20 cm. If composed of an electrically conductive material, the outer surface of the inner probe shaft 18 that could potentially come in contact with tissue is preferably covered with an insulative material (not shown).

The outer probe shaft 20 has a proximal portion 32, a distal portion 34, and a central lumen 36 through which the inner probe shaft 18 is disposed. The outer probe shaft 20 has an outside diameter consistent with its intended use, typically being from 1 mm to 5 mm, usually from 1.3 mm to 4 mm. The central lumen 36 has an inner diameter in the range from 0.7 mm to 4 mm, preferably from 1 mm to 3.5 mm. In the illustrated embodiment, the outer probe shaft 20 is composed of an electrically conductive material, such as metal, e.g., stainless steel. In this case, the outer surfaces of the proximal and distal shaft portions 32, 34 are covered with an insulative material (not shown). The distal shaft portion 34 is affixed to the distal end 28 of the inner probe shaft 18 using suitable means, e.g., soldering or welding. In contrast, the proximal shaft portion 32 is rotatably mounted to the proximal end 26 of the inner probe shaft 18, such that it can be reciprocatably rotated in opposite directions (shown by arrows). As further described below, the proximal shaft portion 32 may also be longitudinally translated relative to the inner probe shaft 18.

The coiled ablation electrode 22 is composed of a coiled metallic element disposed between the proximal and distal portions 32, 34 of the outer probe shaft 20. In the illustrated embodiment, the coiled ablation electrode 22 is formed from the outer probe shaft 20, e.g., by cutting the region of the outer probe shaft 20 between the proximal and distal shaft portions 32, 34. That is, the ablation electrode 22 and proximal and distal shaft portions 32, 34 form a unibody design. The outer probe shaft 20 can be cut to form the coiled ablation electrode 22 using any suitable means, such as chemical or laser cutting. The ablation electrode 22 may be alternately placed between a low-profile collapsed geometry (FIG. 2) and an expanded geometry (FIG. 3).

In the illustrated embodiment, the proximal portion 32 of the outer probe shaft 20 can be rotated about the inner probe shaft 18 in a first direction (shown in FIG. 2) to wind the ablation electrode 22, thereby placing it in a radially collapsed geometry, and rotated about the inner probe shaft 18 in a second opposite direction (shown in FIG. 3) to unwind the ablation electrode 22, thereby placing it in a radially expanded geometry. To facilitate its expansion, the ablation electrode 22 has a shaped spring memory that corresponds with the radially expanded geometry. In this manner, the ablation electrode 22 is urged to expand from the collapsed geometry into the radially expanded geometry by the spring force as the proximal portion 32 of the outer probe shaft 20 is rotated about the inner probe shaft 18 in the first direction to unwind the ablation electrode 22. As can be seen by comparing FIGS. 2 and 3, the ablation electrode 22 is transformed from a coil with a relatively large number of smaller sized windings when in the collapsed geometry to a coil with a relatively small number of larger sized windings when in the radially expanded geometry. In the example, illustrated in FIGS. 2 and 3, there is approximately a 3:1 ratio between the number of windings of the ablation electrode 22 when in the radially collapsed geometry, and the number of windings of the ablation electrode 22 when in the radially expanded geometry. This ratio may be adjusted based on the desired expansion of the ablation electrode 22.

Figure 4:
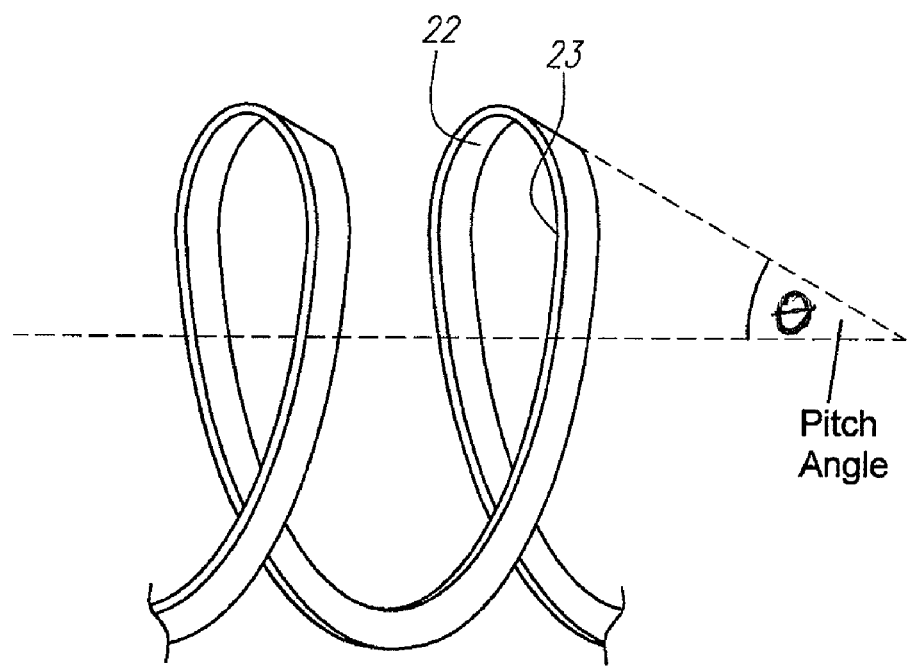
FIG. 4 is a perspective view of an alternative ablation electrode that can be used within the tissue ablation probe of FIG. 2.

The metallic element that makes up the ablation electrode 22 is illustrated in FIGS. 2 and 3 as having a relatively large width. To facilitate the radial expansion of the ablation electrode 22 through tissue, the metallic element may have a relatively small width (e.g., the metallic element can be composed of a fine gauged wire) similar to that illustrated in FIGS. 7A-7D. Alternatively, as illustrated in FIG. 4, the metallic element may be pre-formed to have an angled pitch relative to the longitudinal axis of the ablation electrode 22, so that a leading edge 23 of the metallic element, which may be sharpened, cuts through the tissue as the ablation electrode 22 is expanded.

In the illustrated embodiment, the proximal portion 32 of the outer probe shaft 20 can longitudinally translate relative to the inner probe shaft 18, so that the coil windings of the ablation electrode 22 can move from a closed pitch when in the collapsed geometry, as illustrated in FIG. 2, to an open pitch when in the radially expanded geometry, as illustrated in FIG. 3. In this case, the ablation electrode 22 can be placed in a longitudinally expanded geometry in addition to be placed in the radially expanded geometry. Threads (not shown) may be provided between the proximal shaft portion 32 and the inner probe shaft 18 to facilitate controlled expansion and collapsing of the ablation electrode 22. Alternatively, the proximal portion 32 of the outer probe shaft 20 is not allowed to longitudinally translate relative to the inner probe shaft 18, in which case, the pitch of the ablation electrode 22 will not generally change. That is, if the coil windings of the ablation electrode 22 are closed in the radially collapsed geometry, they will remain closed in the radially expanded geometry.

The handle assembly 24 includes a first handle member 38 mounted to the proximal end 26 of the inner probe shaft 18, and a second handle member 40 mounted to the proximal portion 32 of the outer probe shaft 20. The handle members 38, 40 are preferably composed of a durable and rigid material, such as medical grade plastic, and are ergonomically molded to allow a physician to more easily manipulate the ablation probe 12. The first handle member 38 may be grasped to generally control movement of the ablation probe 12, while the second handle member 40 may be grasped and rotated to rotate the proximal portion 32 of the outer probe shaft 20 about the inner probe shaft 18 to either place the ablation electrode 22 in its expanded geometry or collapsed geometry.

The handle assembly 24 also includes an electrical connector 42 mounted within the first handle member 38. The electrical connector 42 is electrically coupled to the ablation electrode 22, and is configured for mating with the proximal end of the RF cable 16 connected to the RF generator 14. Alternatively, the RF cable 16 may be hardwired within the handle member 36. If the inner probe shaft 18 and outer probe shaft 20 have electrically conductive cores, the electrical connector 42 can be in electrical contact with the core of the inner probe shaft 18, which in turn, can be in electrical contact with the core of the outer probe shaft 20. For example, an uninsulated portion of the outer surface of the inner probe shaft 18 can be in constant contact with an uninsulated portion of the inner surface of the outer probe shaft 20 to ensure that the electrical connector 42 is always in electrical contact with the ablation electrode 22, which is in electrical contact with the core of the outer probe shaft 20. Alternatively, an RF wire (not shown) can be routed from the electrical connector 42 through the inner probe shaft 18, into direct contact with the ablation electrode 22 or into contact with an element, such as a portion of the outer probe shaft 20, in contact with the ablation electrode 22. While the electrical connector 42 is shown as being located within the first handle member 38, it can be located within the second handle member 40, in which case, electrical contact between the electrical connector 42 and the inner probe shaft 18 or any element associated within the inner probe shaft 18 can be obviated.

In the illustrated embodiment, the RF current is delivered to the ablation electrode 22 in a monopolar fashion, which means that current will pass from the electrode 22, which is configured to concentrate the energy flux in order to have an injurious effect on the surrounding tissue, and a dispersive electrode (not shown), which is located remotely from the electrode 22 and has a sufficiently large area (typically 130 $cm^2$ for an adult), so that the current density is low and non-injurious to surrounding tissue. In the illustrated embodiment, the dispersive electrode may be attached externally to the patient, e.g., using a contact pad placed on the patient's flank.

Referring back to FIG. 1, the RF generator 14 may be a conventional RF power supply that operates at a frequency in the range from 200 KHz to 4 MHz, with a conventional sinusoidal or non-sinusoidal wave form. Such power supplies are available from many commercial suppliers, such as Valleylab, Aspen, Bovie, and Ellman. Most general purpose electrosurgical power supplies, however, operate at higher voltages and powers than would normally be necessary or suitable for tissue ablation. Thus, such power supplies would usually be operated at the lower ends of their voltage and power capabilities. More suitable power supplies will be capable of supplying an ablation current at a relatively low voltage, typically below 150V (peak-to-peak), usually being from 50V to 100V. The power will usually be from 20 W to 200 W, usually having a sine wave form, although other wave forms would also be acceptable. Power supplies capable of operating within these ranges are available from commercial vendors, such as Boston Scientific Corporation of San Jose, Calif., who markets these power supplies under the trademarks RF2000™ (100 W) and RF3000™ (200 W).

Figure 5:
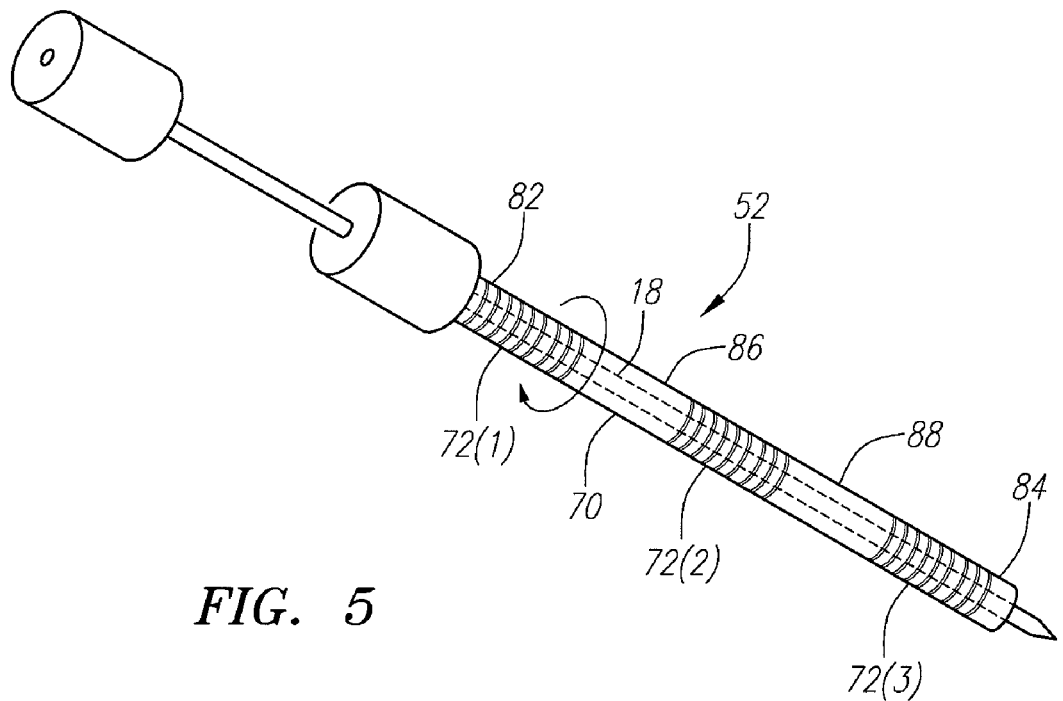
FIG. 5 is a perspective view of another tissue ablation probe that can be used in the tissue ablation system of FIG. 1, wherein ablation electrode are particularly shown in a low-profile collapsed geometry.
Figure 6:
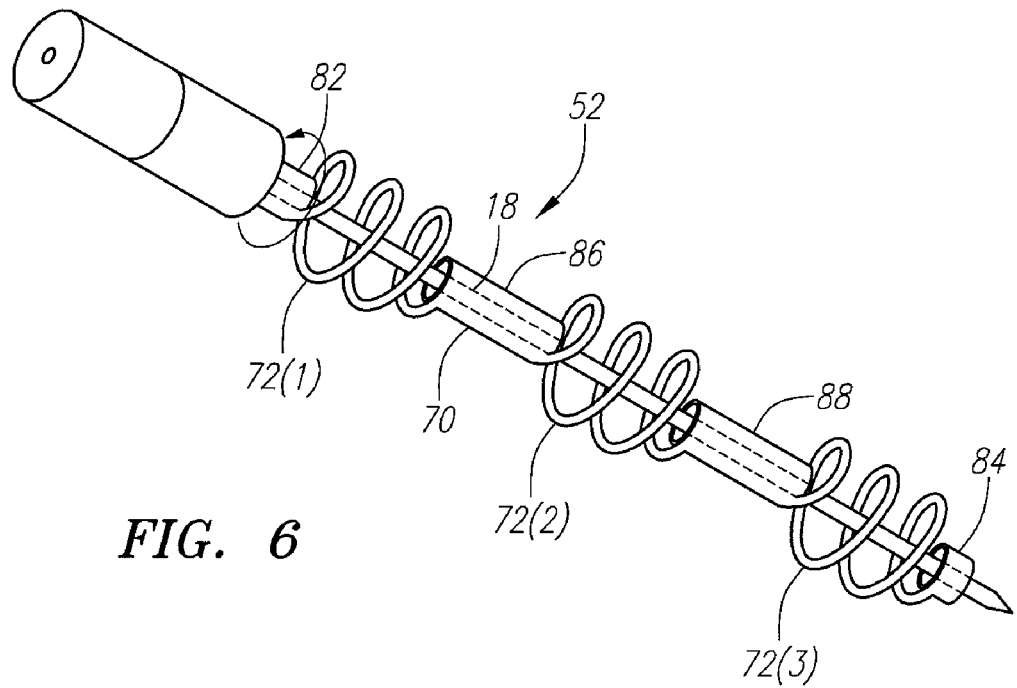
FIG. 6 is a perspective view of the tissue ablation probe of FIG. 5, wherein the ablation electrodes are particularly shown in an expanded geometry.

Referring now to FIGS. 5 and 6, another embodiment of a tissue ablation probe 52, which can be alternatively used in the tissue ablation system of FIG. 1, will now be described. The ablation probe 52 is similar to the previously described ablation probe 12, with the exception that it comprises three coiled ablation electrodes instead of only one.

In particular, the ablation probe 52 has an outer probe shaft 70 that includes a proximal portion 82, a distal portion 84, and two medial portions 86, 88, with a first coiled ablation electrode 72(1) disposed between the proximal portion 82 and the more proximal medial portion 86, a second coiled ablation electrode 72(2) disposed between the two medial portions 86, 88, and a third coiled ablation electrode 72(3) disposed between the more distal medial portion 88 and the distal portion 84. The composition of the outer probe shaft 70 and ablation electrodes 72(1)-(3) may be the same as that of the previously described outer probe shaft 20 and ablation electrode 22, with the ablation electrodes 72(1)-(3) being formed from the outer probe shaft 70.

In a similar manner described above with respect to FIGS. 2 and 3, the ablation electrodes 72(1)-(3), may be alternately placed between a low-profile collapsed geometry (FIG. 5) and an expanded geometry (FIG. 6). In the illustrated embodiment, the proximal portion 82 (as well as the medial portions 86, 88) of the outer probe shaft 70 can be rotated about the inner probe shaft 18 in a first direction (shown in FIG. 5) to simultaneously wind the ablation electrodes 72(1)-(3), thereby placing them in the collapsed geometry, and rotated about the inner probe shaft 18 in a second opposite direction (shown in FIG. 6) to simultaneously unwind the ablation electrodes 72(1)-(3), thereby placing them in the radially expanded geometry. As described above, the ablation electrodes 72(1)-(3) may optionally be self-expanding and include sharpened edges that facilitate their expansion through tissue. The expanded coil windings of the ablation electrodes 72(1)-(3) may also be open-pitched, as illustrated in FIG. 6, in which case, the proximal portion 82 and medial portions 86, 88 of the outer probe shaft 70 will longitudinally move relative to the inner probe shaft 18, or closed-pitched, in which case, the proximal portion 82 and medial portions 86, 88 of the outer probe shaft 70 may not longitudinally move relative to the inner probe shaft 18.

Connection of the electrical connector 42 to the ablation electrodes 72(1)-(3) may be accomplished in the same manner described above. Optionally, the ablation electrodes 72(1)-(3) may be configured in a bipolar manner. For example, a positive pin (not shown) of the electrical connector 42 can be electrically coupled to the first and third ablation electrodes 72(1), 72(3), while a ground pin (not shown) of the electrical connector 42 can be electrically coupled to the second ablation electrode 72(2). In this case, the RF current is delivered to the electrodes 72(1)-(3) in a bipolar fashion, which means that current will pass between "positive" and "negative" electrodes, and in this exemplary case, from the first and third ablation electrodes 72(1), 72(3) to the second ablation electrode 72(2).

Having described the structure of the tissue ablation system 10, its operation in treating targeted tissue will now be described. The treatment region may be located anywhere in the body where hyperthermic exposure may be beneficial. Most commonly, the treatment region will comprise a solid tumor within an organ of the body, such as the liver, kidney, pancreas, breast, prostrate (not accessed via the urethra), and the like. The volume to be treated will depend on the size of the tumor or other lesion, typically having a total volume from 1 cm$^3$ to 150 cm$^3$, and often from 2 cm$^3$ to 35 cm$^3$. The peripheral dimensions of the treatment region may be regular, e.g., spherical or ellipsoidal, but will more usually be irregular. The treatment region may be identified using conventional imaging techniques capable of elucidating a target tissue, e.g., tumor tissue, such as ultrasonic scanning, magnetic resonance imaging (MRI), computer-assisted tomography (CAT), fluoroscopy, nuclear scanning (using radiolabeled tumor-specific probes), and the like. Preferred is the use of high resolution ultrasound of the tumor or other lesion being treated, either intraoperatively or externally.

Figure 7A:
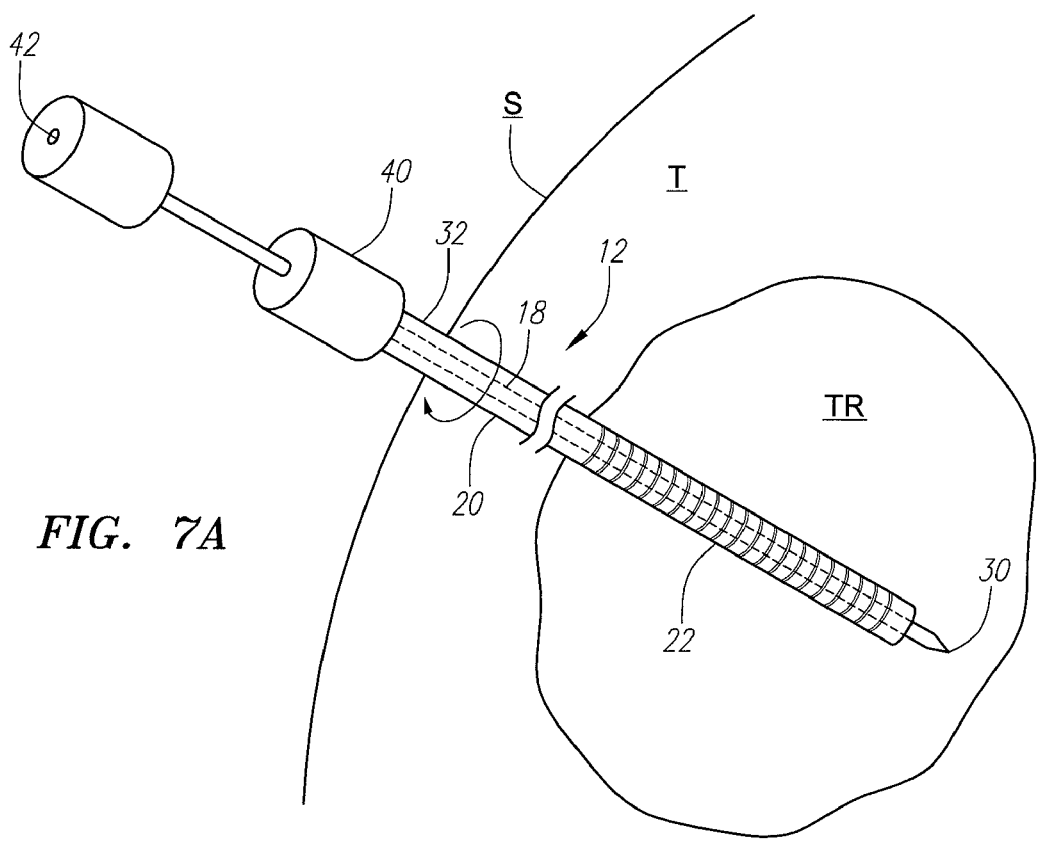
FIGS. 7A-7D are cross-sectional views of one preferred method of using the tissue ablation system of FIG. 1 to treat tissue.

Referring now to FIGS. 7A-7D, the operation of the tissue ablation system 10 is described in treating a treatment region TR within tissue T located beneath the skin or an organ surface S of a patient. Although the ablation probe 12 is shown in this example, the ablation probe 52 can also be used in the same manner. First, while the ablation electrode 22 is in a low-profile collapsed geometry, the ablation probe 12 is introduced within the tissue T, such that the electrode 22 is located in the center of the treatment region TR, as shown in FIG. 7A. If the electrode 22 is self-expanding, the proximal portion 32 of the outer probe shaft 20 can be grasped via the second handle member 40 and stabilized relative to the inner probe shaft 18, so that the ablation electrode 22 does not self-expand as it is being introduced through the tissue T. In the illustrated method, the ablation probe 12 is introduced through the tissue T without the aid of a delivery cannula. In this case, the rigidity and sharpened distal tip 30 of the inner probe shaft 18 facilitates introduction through the tissue T.

Figure 7B:
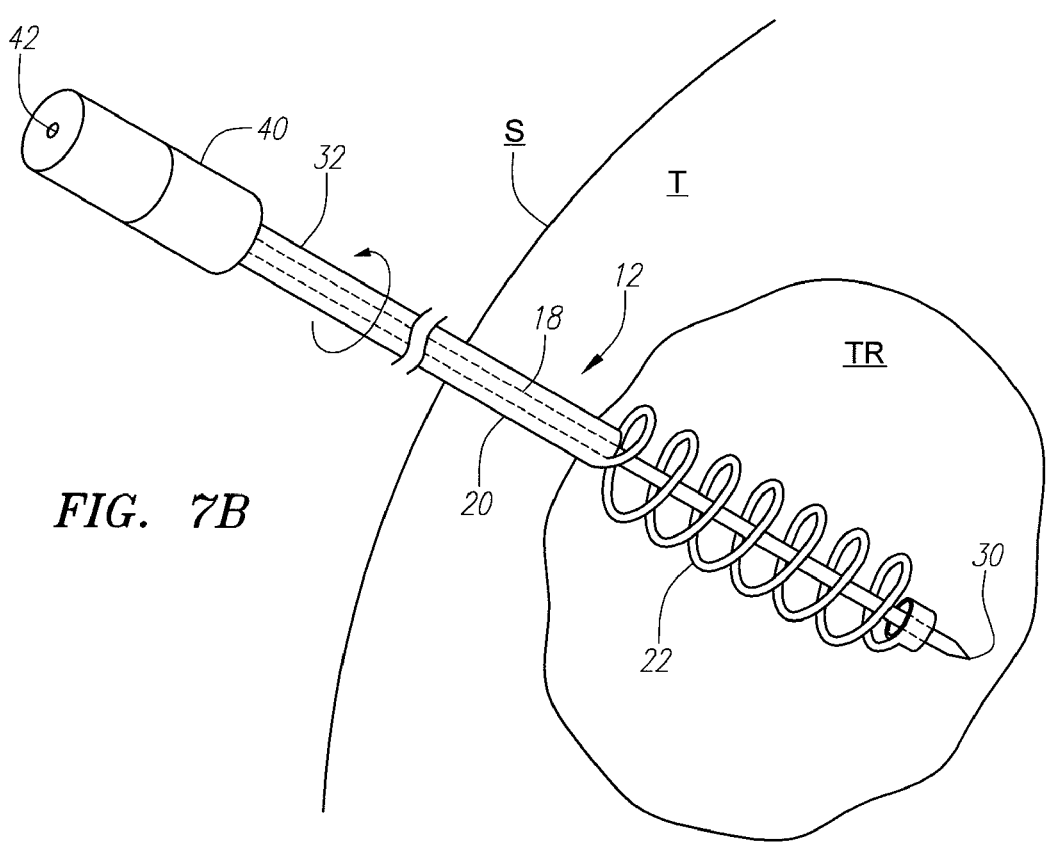
Figure 7C:
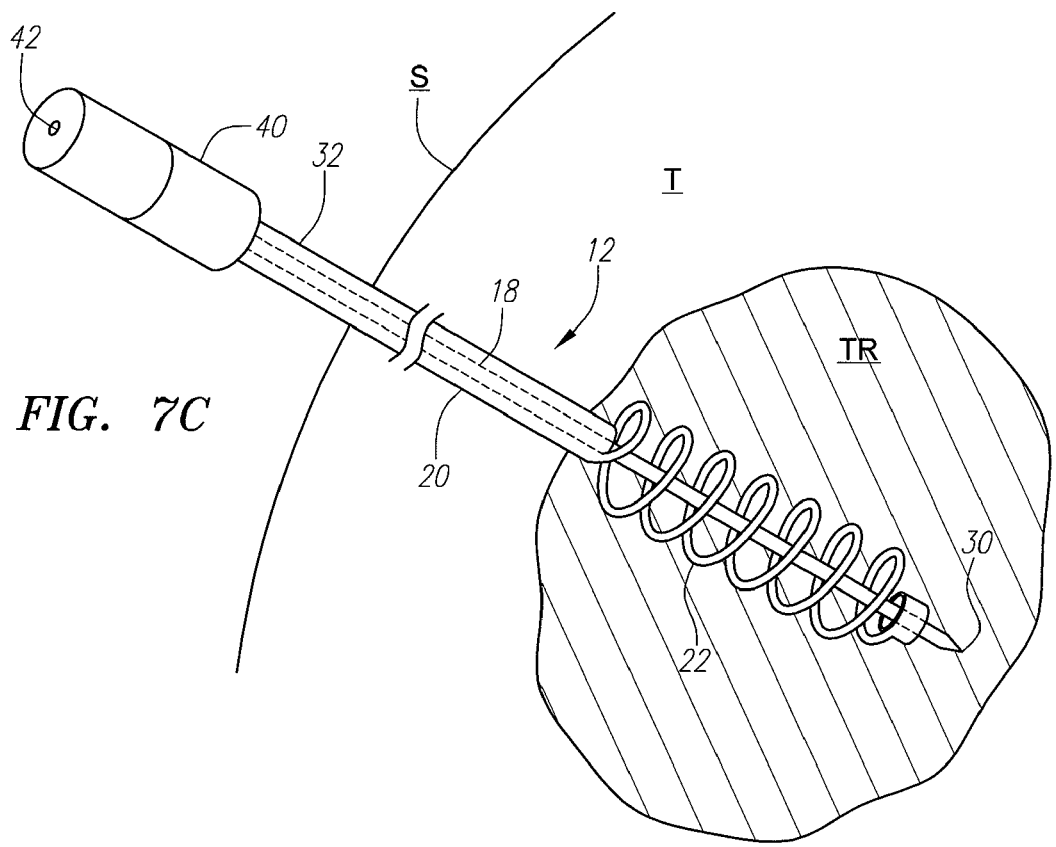
Figure 7D:
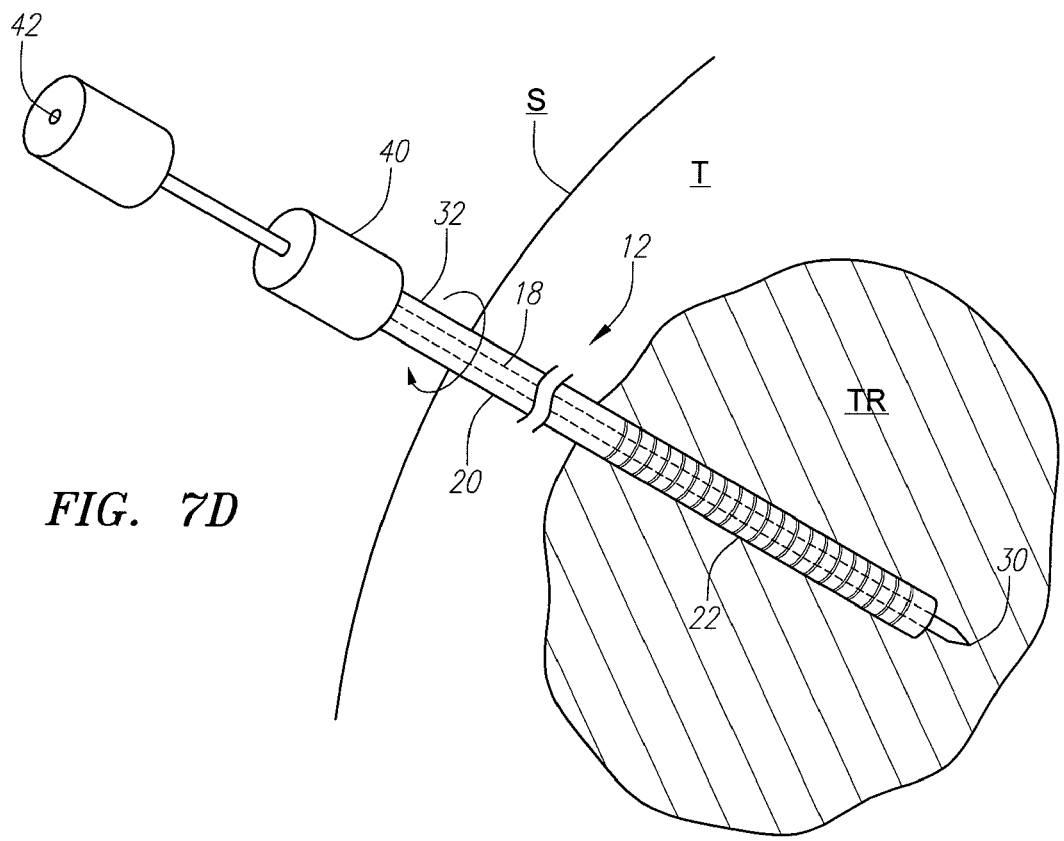

After the ablation probe 12 is properly placed, the proximal portion 32 of the outer probe shaft 20 is rotated in the second direction, thereby placing the ablation electrode 22 in the radially expanded geometry, as illustrated in FIG. 7B. If the ablation electrode 22 is self-expanding, the proximal portion 32 need only be released to allow it to rotate in the first direction in response to the expanding spring force of the ablation electrode 22. The RF generator 14 is then connected to the electrical connector 42 on the ablation probe 12 via the cable 16, and then operated to ablate the treatment region TR, as illustrated in FIG. 7C. Next, the proximal portion 32 of the outer probe shaft 20 is rotated in the first opposite direction, thereby placing the ablation electrode 22 back into the collapsed geometry, as illustrated in FIG. 7D. If the electrode 22 is self-expanding, the proximal portion 32 of the outer probe shaft 20 can be grasped and stabilized relative to the inner probe shaft 18 to maintain the ablation electrode in the collapsed geometry as the ablation probe 12 is removed from the patient.

Figure 8A:
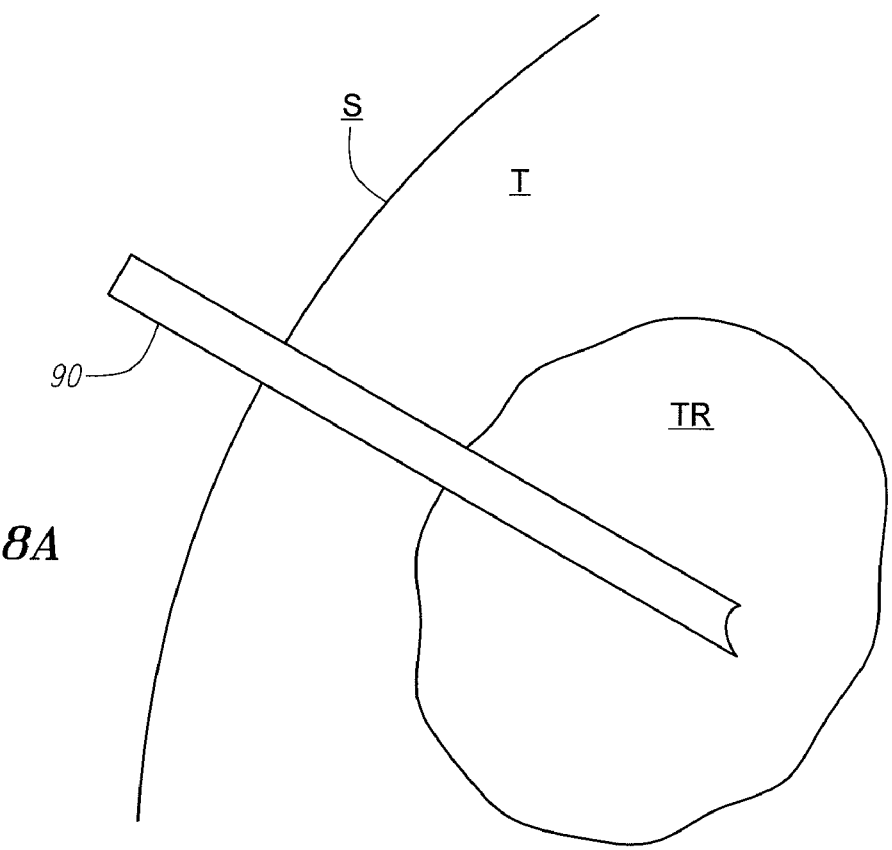
FIGS. 8A and 8B are cross-sectional views of an alternative preferred method of using the tissue ablation system of FIG. 1 to treat tissue.
Figure 8B:
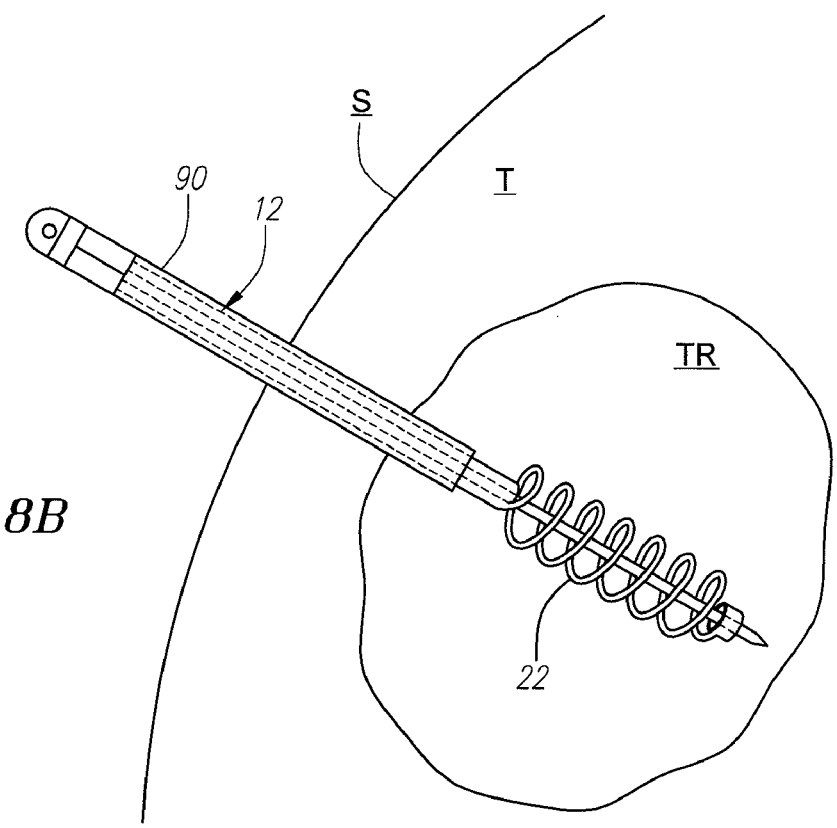

Although the ablation probe 12 has been described as being introduced through the tissue T without a cannula, alternatively, the ablation probe 12 can be introduced through the tissue T with the aid of a cannula 90, as illustrated in FIG. 8A. In this case, the cannula 90 may have a sharpened tip, e.g., in the form of a needle, to facilitate introduction to the treatment region TR. In such cases, it is desirable that the cannula 90 or needle be sufficiently rigid, i.e., have a sufficient column strength, so that it can be accurately advanced through tissue T. In other cases, the cannula 90 may be introduced using an internal stylet that is subsequently exchanged for the ablation probe 12. In this latter case, the cannula 90 can be relatively flexible, since the initial column strength will be provided by the stylet. More alternatively, a component or element may be provided for introducing the cannula 90 through the tissue T. For example, a conventional sheath and sharpened obturator (stylet) assembly can be used to initially access the tissue T. The assembly can be positioned under ultrasonic or other conventional imaging, with the obturator/stylet then removed to leave an access lumen through the sheath. The cannula 90 and ablation probe 12 can then be introduced through the sheath lumen, so that the distal end of the cannula 90 advances from the sheath into the treatment region TR. Once the cannula 90 is properly placed, the ablation probe 12 can be advanced distally relative to the cannula 90 until the ablation electrode 22 deploys out of the distal end of the cannula 90. In the same manner described above, the ablation electrode 22 can then be placed into the radially expanded geometry, as illustrated in FIG. 8B. Notably, if the ablation electrode 22 is self-expanding, the compressive force applied to the electrode by the cannula 90 will maintain the electrode 22 within it low-profile collapsed geometry until deployed out from the cannula 90, after which the ablation electrode 22 will automatically expand.

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed is:

1. A probe for ablating tissue, comprising:
an inner probe shaft;
an outer probe shaft disposed around the inner probe shaft, the outer probe shaft having a distal portion fixably mounted to the inner probe shaft, and a proximal portion rotatably mounted to the inner probe shaft; and a coiled ablation electrode disposed between the proximal portion and the distal portion, the electrode configured for unwinding when the proximal portion rotates about the inner probe shaft in one direction, thereby placing the electrode in a radially expanded geometry, and configured for winding when the proximal portion rotates about the inner probe shaft in another opposite direction, thereby placing the electrode in a radially collapsed geometry, wherein the electrode comprises a plurality of windings, each one of the windings having a sharpened leading edge and a flat width extending between the leading edge and a trailing edge, wherein the flat width is pitched relative to a longitudinal axis of the electrode.

2. The probe of claim 1, wherein the inner probe shaft is rigid.

3. The probe of claim 1, wherein the inner probe shaft has a tissue penetrating distal tip.

4. The probe of claim 1, wherein the proximal portion is configured for longitudinally translating in a proximal direction relative to the inner probe shaft, thereby placing the electrode in a longitudinally expanded geometry.

5. The probe of claim 1, wherein the electrode is configured for unwinding in response to rotation of the proximal portion in the one direction, and configured for winding in response to rotation of the proximal portion in the other direction.

6. The probe of claim 1, wherein the electrode has a shaped memory corresponding to the radially expanded geometry.

7. The probe of claim 1, wherein the proximal portion, distal portion, and electrode form a unibody design.

8. The probe of claim 1, further comprising an electrical connector electrically coupled to the electrode.

9. The probe of claim 1, wherein the outer probe shaft has a medial portion disposed between the proximal and distal portions, the electrode is disposed between the proximal portion and the medial portion, the outer probe shaft further comprising another coiled ablation electrode disposed between the medial portion and the distal portion, the other electrode configured for unwinding when the proximal portion rotates about the inner probe shaft in the one direction, thereby placing the other electrode in a radially expanded geometry, and configured for winding when the proximal portion rotates about the inner probe shaft in the other opposite direction, thereby placing the other electrode in a radially collapsed geometry.

10. A tissue ablation system, comprising:
the probe of claim 1; and
a radio frequency (RF) source operably coupled to the electrode.

11. A method of treating tissue, comprising:
introducing the probe of claim 1 into contact with the tissue while the electrode is in the radially collapsed geometry;
placing the electrode in the radially expanded geometry; and
conveying radio frequency (RF) energy from the radially expanded electrode, thereby creating an ablation lesion within the tissue.

12. The method of claim 11, further comprising rotating the proximal portion in the one direction to place the electrode in the radially expanded geometry.

13. The method of claim 11, further comprising displacing the proximal portion in a proximal direction relative to the inner probe shaft to place the electrode in a longitudinally expanded geometry.

14. The method of claim 11, wherein the tissue is a tumor.

15. The probe of claim 1, wherein, when the electrode is in the radially collapsed geometry, a diameter of the electrode is substantially equal to a diameter of the distal and proximal portions of the outer probe shaft.

16. The probe of claim 1, wherein a ratio between a number of windings of the ablation electrode when in the radially collapsed geometry, and a number of windings of the ablation electrode when in the radially expanded geometry is approximately 3:1.

17. The probe of claim 1, wherein the outer probe shaft comprises an electrically conductive material.

18. The probe of claim 17, wherein outer surfaces of the distal and proximal portions of the outer probe shaft comprise an insulative covering.

19. The probe of claim 1, further comprising a first handle member mounted to a proximal end of the inner probe shaft and a second handle member mounted to the proximal portion of the outer probe shaft, wherein the second handle member is configured for rotational and axial translation relative to the first handle member.

20. The probe of claim 9, further comprising a third coiled ablation electrode, wherein the probe is configured for bipolar ablation.

* * * * *